US006265154B1

(12) United States Patent
Kroeger et al.

(10) Patent No.: US 6,265,154 B1
(45) Date of Patent: *Jul. 24, 2001

(54) NUCLEIC ACID PRIMERS AND PROBES FOR DETECTING ONCOGENIC HUMAN PAPILLOMAVIRUSES

(75) Inventors: Paul E. Kroeger, Lindenhurst; Klara Abravaya, Wilmette; Jacek J. Gorzowski, Round Lake Park; Robert J. Hoenle, Crystal Lake; Jennifer J. Moore, Chicago, all of IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/739,103

(22) Filed: Oct. 25, 1996

(51) Int. Cl.[7] .............................. C12Q 1/68; C12P 19/34; C07H 21/04
(52) U.S. Cl. ........................ 435/6; 435/91.2; 536/24.31
(58) Field of Search .................................. 435/5, 6, 91.2, 435/810; 536/24.3, 24.32, 24.33; 935/8, 17, 77, 78

(56) References Cited

U.S. PATENT DOCUMENTS

| 5,364,758 | 11/1994 | Meijer et al. | 435/5 |
| 5,447,839 | * 9/1995 | Manos et al. | 435/5 |
| 5,527,898 | * 6/1996 | Bauer et al. | 536/24.3 |

FOREIGN PATENT DOCUMENTS

| 0489442 | 6/1992 | (EP) . |
| 9001564 | 2/1990 | (WO) . |
| 9522626 | 8/1995 | (WO) . |

OTHER PUBLICATIONS

Melchers, W., et. al., "Increased Detection Rate of Human Papillomavirus in Cervical Scrapes by the Polymerase Chain Reaction as Compared to Modified FISH and Southern–Blot Analysis", *Journ. Of Med. Virology*, 27(4):329–335 (1989).

Bernard, C., et al., "Detection of human papillomavirus by in situ polymerase chain reaction in paraffin–embedded cervical biopsies", *Molecular and Cellular Probes*, 8:337–343 (1994).

Husman, A–M, et al., "The use of general primers GP5 and GP6 elongated at their 3' ends with adjacent highly conserved sequences improves human papillomavirus detection by PCR", *Journal of General Virology*, 76:1057–1062 (1995).

Jacobs, M.V., et al., "Group–Specific Differentiation between High– and Low–Risk Human Papillomavirus Genotypes by General Primer–Mediated PCR and Two Cocktails of Oligonucleotide Probes", *Journal of Clinical Microbiology*, 33(4):901–905 (1995).

Snijders, P.J.F., et al., "The use of general primers in the polymerase chain reaction permits the detection of a broad spectrum of human papillomavirus genotypes", *Journal of General Virology*, 71:173–181 (1990).

\* cited by examiner

*Primary Examiner*—Lisa B. Arthur
(74) *Attorney, Agent, or Firm*—Paul D. Yasger; David J. Schodin

(57) ABSTRACT

Probe sequences that are useful for detecting oncogenic HPV types 16, 18, 31, 33, 35, 39, 45, 51, 52, 56, 58, 59 and 68 are herein provided. These sequences can be used in hybridization assays or amplification based assays designed to detect the presence of these oncogenic HPV types in a test sample. Additionally, the sequences can be provided as part of a kit.

6 Claims, No Drawings

NUCLEIC ACID PRIMERS AND PROBES FOR DETECTING ONCOGENIC HUMAN PAPILLOMAVIRUSES

FIELD OF THE INVENTION

The present invention relates to human papillomaviruses and, in particular, it relates to oligonucleotides for detecting human papillomaviruses in a test sample.

BACKGROUND OF THE INVENTION

To date, approximately seventy different human papillomavirus (HPV) types have been discovered. HPV is interesting from a diagnostic standpoint because several of the presently known HPV types have been linked to the development of cervical cancer. As with any form of cancer, early detection is critical to successfully treating the disease. Because certain HPV strains are associated with the development of cervical cancer, detecting HPV in an appropriate sample may provide the best means for the early detection of cervical cancer.

The polymerase chain reaction in combination with Southern blot analysis has been the prevailing method for detecting particular types of HPV in a test sample. In particular Snijders, P. J. F., et. al., J. of Gen. Virol., Vol. 71, pp.173–181 (1990) exemplifies such technology where amplification primers are employed to generate multiple copies of a sequence within the HPV genome and radiolabeled DNA probes specific for a particular HPV type are employed to detect and thereby determine the particular HPV type present in the test sample. Unfortunately, Southern blotting is a relatively labor intensive and time consuming process especially when attempting to detect multiple different HPV types. Accordingly, there is a need for methods and reagents suitable for quickly and accurately determining whether or not one or several of the HPV types associated with cervical cancer are present in a test sample.

SUMMARY OF THE INVENTION

The present invention provides oligonucleotides that can be used to specifically detect oncogenic HPV types 16, 18, 31, 33, 35, 39, 45, 51, 52, 56, 58, 59 and 68 (hereinafter "oncogenic HPV types"). These oligonucleotides are designated SEQ ID NO 4 and its complement SEQ ID NO 5; SEQ ID NO 7 and its complement SEQ ID NO 8; SEQ ID NO 10 and its complement SEQ ID NO 11; SEQ ID NO 13 and its complement SEQ ID NO 14; SEQ ID NO 16 and its complement SEQ ID NO 17; SEQ ID NO 19 and its complement SEQ ID NO 20; SEQ ID NO 22 and its complement SEQ ID NO 23; SEQ ID NO 25 and its complement SEQ ID NO 26; SEQ ID NO 28 and its complement SEQ ID NO 29; SEQ ID NO 31 and its complement SEQ ID NO 32; SEQ ID NO 34 and its complement SEQ ID NO 35; SEQ ID NO 37 and its complement SEQ ID NO 38; as well as SEQ ID NO 40 and its complement SEQ ID NO 41. Preferred are cocktails of these probes comprising two or more of the above oligonucleotides.

Preferably, the oligonucleotides are employed as hybridization probes to hybridize with and detect target sequences for which they are specific. Thus, methods provided by the present invention include hybridization assays as well as amplification based assays. According to one method, a method of detecting the presence of at least one oncogenic HPV type in a test sample comprises the steps of (a) contacting the test sample with one or more of the sequences listed above; and (b) detecting hybridization between at least one of the above sequences and an oncogenic HPV target sequence as an indication of the presence of at least one oncogenic HPV type in the test sample.

According to another embodiment, a method for detecting the presence of at least one oncogenic HPV type in a test sample comprises the steps of (a) forming a reaction mixture comprising nucleic acid amplification reagents, a test sample containing an oncogenic HPV target sequence, at least one (and preferably two) primer(s) capable of amplifying an HPV target sequence designated herein as SEQ ID NO.3, SEQ ID NO. 6, SEQ ID NO. 9, SEQ ID NO. 12, SEQ ID NO. 15, SEQ ID NO. 18, SEQ ID NO. 21, SEQ ID NO. 24, SEQ ID NO. 27, SEQ ID NO. 30, SEQ ID 35 NO. 33, SEQ ID NO. 36, and SEQ ID NO. 39 and one or more oligonucleotides selected from the group consisting of SEQ ID NO 4, SEQ ID NO 7, SEQ ID NO. 10, SEQ ID NO 13, SEQ ID NO 16, SEQ ID NO 19, SEQ ID NO 22, SEQ ID NO 25, SEQ ID NO 28, SEQ ID NO 31, SEQ ID NO 34, SEQ ID NO 37, SEQ ID NO 40, and their respective complements; (b) subjecting the mixture to hybridization conditions to produce at least one nucleic acid sequence complementary to the target sequence; (c) hybridizing one or more oligonucleotides to the nucleic acid sequence complementary to the target sequence, so as to form at least one complex comprising the oligonucleotide and the complementary nucleic acid sequence; and (d) detecting the so-formed complex as an indication of the presence of at least one oncogenic HPV type in the sample.

According to another embodiment, the invention provides kits which comprise a set of oligonucleotide primers, amplification reagents and at least one, and preferably at least two, of the oligonucleotides designated as SEQ ID NO. 4, SEQ ID NO. 5, SEQ ID NO. 7, SEQ ID NO. 8, SEQ ID NO. 10, SEQ ID NO. 11, SEQ ID NO. 13, SEQ ID NO. 14, SEQ ID NO. 16, SEQ ID NO. 17, SEQ ID NO. 19, SEQ ID NO. 20, SEQ ID NO. 22, SEQ ID NO. 23, SEQ ID NO. 25, SEQ ID NO. 26, SEQ ID NO. 28, SEQ ID NO. 29, SEQ ID NO. 31, SEQ ID NO. 32, SEQ ID NO. 34, SEQ ID NO. 35, SEQ ID NO. 37, SEQ ID NO. 38, SEQ ID NO. 40 and SEQ ID NO. 41.

DETAILED DESCRIPTION OF THE INVENTION

As previously mentioned, the present invention provides oligonucleotides (hereinafter "oligos" or "probes"), methods for using the probes and kits containing the probes, all of which can be employed to specifically detect oncogenic HPV types (i.e. HPV types 16, 18, 31, 33, 35, 39, 45, 51, 52, 56, 58, 59 and 68). The probes provided herein can be employed as primers in an amplification reaction but preferably are employed as hybridization probes because each of the probes is specific for at least one HPV type and in one case (SEQ ID NO. 34) two HPV types. Advantageously, all of the probes hybridize within an approximately 140 bp region of the L1 gene found in the HPV genome. Thus, while the probes individually can be used to detect the oncogenic HPV type(s) for which they are specific, a cocktail comprising two or more of the oligos can be employed to detect several HPV types at once. This is particularly advantageous in an amplification reaction setting where all, more or part of the approximately 140 bp region can be amplified and the amplified product can be contacted with a cocktail of probes to determine the presence of at least one of the oncogenic HPV types in the test sample. Accordingly, a single amplification reaction can be the basis for detecting multiple HPV types. Table 1 below provides the SEQ ID NOs. of the oligos provided herein, the sequences and the HPV type(s) that they specifically detect.

| SEQ ID NO. | SEQUENCE 5' -> 3' | HPV TYPE SPECIFICITY |
| --- | --- | --- |
| 4 | GCTGCCATAT CTACTTCA | 16 |
| 5 | TGAAGTAGAT ATGGCAGC | 16 |
| 7 | GTAGCATCAT ATTGCC | 18 |
| 8 | GGCAATATGA TGCTAC | 18 |
| 10 | GCAATTGCAA ACAGTGAT | 31 |
| 11 | ATCACTGTTT GCAATTGC | 31 |
| 13 | ATGCACACAA GTAACTAGT | 33 |
| 14 | A6TAGTTACT TGTGTGCAT | 33 |
| 16 | CTGCTGTGTC TTCTAGTG | 35 |
| 17 | CACTAGAAGA CACAGCAG | 35 |
| 19 | CTCTATAGAG TCTTCCATAC C | 39 |
| 20 | GGTATGGAAG ACTCTATAGA G | 39 |
| 22 | CTACACAAAA TCCTGTG | 45 |
| 23 | CACAGGATTT TGTGTAG | 45 |
| 25 | CGGTTTCCCC AACAT | 51 |
| 26 | ATGTTGGGGA AACCG | 51 |
| 28 | GTGCTGAGGT TAAAAAG | 52 |
| 29 | CTTTTTAACC TCAGCAC | 52 |
| 31 | CTACAGAACA GTTAAGTAA | 56 |
| 32 | TTACTTAACT GTTCTGTAG | 56 |
| 34 | AACTAAGGAA GGTACAT | 58/33 |
| 35 | ATGTACCTTC CTTAGTT | 58/33 |
| 37 | CTACTACTCT CTATTCCTAA TG | 59 |
| 38 | CATTAGGAAT AGAGAGTAGT AG | 59 |
| 40 | CTTTGTCTAC TACTACTGA | 68 |
| 41 | TCAGTAGTAG TAGACAAAG | 68 |

The probes disclosed herein may comprise deoxyribonucleic acid (DNA), ribonucleic acid (RNA) or nucleic acid analogs such as uncharged nucleic acid analogs including but not limited to peptide nucleic acids (PNAs) which are disclosed in International Patent Application WO 92/20702 or morpholino analogs which are described in U.S. Pat. Nos. 5,185,444, 5,034,506, and 5,142,047 all of which are herein incorporated by reference. Such sequences can routinely be synthesized using a variety of techniques currently available. For example, a sequence of DNA can be synthesized using conventional nucleotide phosphoramidite chemistry and the instruments available from Applied Biosystems, Inc, (Foster City, Calif.); DuPont, (Wilmington, Del.); or Milligen, (Bedford, Mass.). Similarly, and when desirable, the sequences can be labeled using methodologies well known in the art such as described in U.S. Pat. Nos. 5,464,746; 5,424,414; and 4,948,882 all of which are herein incorporated by reference.

The term "label" as used herein means a molecule or moiety having a property or characteristic which is capable of detection. A label can be directly detectable, as with, for example, radioisotopes, fluorophores, chemiluminophores, enzymes, colloidal particles, fluorescent microparticles and the like; or a label may be indirectly detectable, as with, for example, specific binding members. It will be understood that directly detectable labels may require additional components such as, for example, substrates, triggering reagents, light, and the like to enable detection of the label. When indirectly detectable labels are used, they are typically used in combination with a "conjugate". A conjugate is typically a specific binding member which has been attached or coupled to a directly detectable label. Coupling chemistries for synthesizing a conjugate are well known in the art and can include, for example, any chemical means and/or physical means that does not destroy the specific binding property of the specific binding member or the detectable property of the label. As used herein, "specific binding member" means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; complementary nucleotide sequences; enzyme cofactors or substrates and enzymes; and the like.

Generally, the probes provided herein can be employed to detect the presence of an oncogenic HPV type in a test sample by contacting a test sample with at least one of the sequences provided herein under hybridizing conditions, and detecting hybridization between an HPV target sequence and at least one of the sequences designated herein as SEQ ID NO 4, SEQ ID NO 5, SEQ ID NO 7, SEQ ID NO 8, SEQ ID NO 10, SEQ ID NO 11, SEQ ID NO 13, SEQ ID NO 14, SEQ ID NO 16, SEQ ID NO 17, SEQ ID NO 19, SEQ ID NO 20, SEQ ID NO 22, SEQ ID NO 23, SEQ ID NO 25, SEQ ID NO 26, SEQ ID NO 28, SEQ ID NO 29, SEQ ID NO 31, SEQ ID NO 32, SEQ ID NO 34, SEQ ID NO 35, SEQ ID NO 37, SEQ ID NO 38, SEQ ID NO 40 and SEQ ID NO 41. Several well known methods for detecting hybridization can be employed according to the present invention and may include, for example, the use of gels and stains or detecting a label associated with one or more of the sequences provided herein after performing, for example, a dot blot or amplification reaction.

The term "test sample" as used herein, means anything suspected of containing a target sequence. The test sample can be derived from any biological source and can be used (i) directly as obtained from the source or (ii) following a pre-treatment to modify the character of the sample. Thus, the test sample can be pre-treated prior to use by, for example, disrupting cells, preparing liquids from solid materials, diluting viscous fluids, filtering liquids, distilling liquids, concentrating liquids, inactivating interfering components, adding reagents, purifying nucleic acids, and the like. Typically, the test sample will be or be derived from cervical scrapes or similar samples.

A "target sequence" as used herein means a nucleic acid sequence that is detected, amplified, both amplified and detected or otherwise is complementary to one of the probes herein provided. Additionally, while the term target sequence is sometimes referred to as single stranded, those skilled in the art will recognize that the target sequence may actually be double stranded.

"Hybridization" or "hybridizing" conditions are defined generally as conditions which promote annealing between complementary nucleic acid sequences or annealing and extension of one or more nucleic acid sequences. It is well known in the art that such annealing is dependent in a rather predictable manner on several parameters, including temperature, ionic strength, sequence length, complementarity, and G:C content of the sequences. For example, lowering the temperature in the environment of complementary nucleic acid sequences promotes annealing. For any given set of sequences, melt temperature, or Tm, can be estimated by any of several known methods. Typically, diagnostic applications utilize hybridization temperatures which are close to (i.e. within 10° C.) the melt temperature. Ionic strength or "salt" concentration also impacts the melt temperature, since small cations tend to stabilize the formation of duplexes by negating the negative charge on the phosphodiester backbone. Typical salt concentrations depend on the nature and valency of the cation but are readily understood by those skilled in the art. Similarly, high G:C content and increased sequence length are also known to stabilize duplex formation because G:C pairings involve 3 hydrogen bonds where A:T pairs have just two, and because longer sequences have more hydrogen bonds holding the sequences together. Thus, a high G:C content and longer sequence lengths impact the hybridization conditions by elevating the melt temperature.

Once sequences are selected for a given diagnostic application, the G:C content and length will be known and can be accounted for in determining precisely what hybridization conditions will encompass. Since ionic strength is typically optimized for enzymatic activity, the only parameter left to vary is the temperature. Generally, the hybridization temperature is selected close to or at the Tm of the primers or probe. Thus, obtaining suitable hybridization conditions for a particular primer, probe, or primer and probe set is well within ordinary skill of one practicing this art.

The sequences provided herein also can be used as amplification primers according to amplification procedures well known in the art. Such reactions include, but are not intended to be limited to, the polymerase chain reaction (PCR) described in U.S. Pat. Nos. 4,683,195 and 4,683,202, the ligase chain reaction (LCR) described in EP-A-320 308, and gap LCR (GLCR) described in U.S. Pat. No. 5,427,930 all of which are herein incorporated by reference.

According to a preferred embodiment, the probes are employed in the "oligonucleotide hybridization PCR" (variably referred to herein as "OH PCR") amplification reaction as described in U.S. patent application Ser. No. 08/514,704, filed Aug. 14, 1995, that is herein incorporated by reference. Briefly, the reagents employed in the preferred method comprise at least one amplification primer (preferably two) and at least one probe, as well as other reagents for performing an amplification reaction.

The primer sequence is employed to prime extension of a copy of a target sequence (or its complement) and is labeled with either a capture label or a detection label. The probe sequence is used to hybridize with the sequence generated by the primer sequence, and typically hybridizes with a sequence that does not include the primer sequence or its exact complement. Similarly to the primer sequence, the probe sequence is also labeled with either a capture label or a detection label with the caveat that when the primer is labeled with a capture label, the probe is labeled with a detection label and vice versa. Detection labels have the same definition as "labels" previously defined and "capture labels" are typically used to separate extension products, and probes associated with any such products, from other amplification reactants. Specific binding members (as previously defined) are well suited for this purpose. Also, probes used according to the OH PCR method are preferably blocked at their 3' ends so that they are not extended under hybridization conditions. Methods for preventing extension of a probe are well known and are a matter of choice for one skilled in the art. For example, adding a phosphate group or label to the 3' end of the probe generally will suffice for purposes of blocking extension of the probe.

"Other reagents for performing an amplification reaction" or "nucleic acid amplification reagents" include reagents which are well known and may include, but are not limited to, an enzyme having polymerase activity, enzyme cofactors such as magnesium; salts; nicotinamide adenine dinucleotide (NAD); and deoxynucleotide triphosphates (dNTPs) such as for example deoxyadenine triphosphate, deoxyguanine triphosphate, deoxycytosine triphosphate and deoxythymine triphosphate.

The OH PCR method generally comprises the steps of (a) forming a reaction mixture comprising nucleic acid amplification reagents, one or more probes herein provided, at least one amplification primer and a test sample suspected of containing a target sequence; (b) subjecting the mixture to hybridization conditions to generate at least one copy of a nucleic acid sequence complementary to the target sequence; (c) hybridizing the probe to the nucleic acid sequence complementary to the target sequence, so as to form a hybrid comprising the probe and the nucleic acid sequence complementary to the target sequence; and (d) detecting the hybrid as an indication of the presence of at least one oncogenic HPV type in the sample. It will be understood that step (b) of the above method can be repeated several times prior to step (c), by thermal cycling the reaction mixture as is well known in the art.

According to the above method, it is preferable to select primers, probes and reaction conditions such that the probe sequence has a lower melt temperature than the primer sequences so that upon placing the reaction mixture under hybridization conditions copies of the target sequence or its complement are produced at a temperature above the Tm of the probe. After such copies are synthesized, they are denatured and the mixture is cooled to enable the formation of hybrids between the probes and any copies of the target or its complement. The rate of temperature reduction from the denaturation temperature down to a temperature at which the probes will bind to single stranded copies is preferably quite rapid (for example 8 to 15 minutes) and particularly through the temperature range in which an enzyme having polymerase activity is active for primer extension. Such a rapid cooling favors copy sequence/probe hybridization rather that primer/copy sequence hybridization and extension.

Upon formation of the copy sequence/probe hybrids, the differential labels (i.e. capture and detection labels) on the copy sequence and probe can be used to separate and detect such hybrids. Preferably, detection is performed according to the protocols used by the commercially available Abbott LCx® instrumentation (Abbott Laboratories; Abbott Park, Ill.).

Thus, keeping the preferred method in mind, preferred reaction mixtures include one or more of the probes of the present invention and a primer or set of primers that prime extension of copies of target sequences having SEQ ID NOs. 3, 6, 9, 12, 15, 18, 21, 24, 27, 30, 33, 36, and 39 (i.e. at least one primer sequence and at least one probe sequence complementary to the extension product of the primer). SEQ ID NO. 1 and/or SEQ ID NO. 2 are exemplary sequences suitable for generating copies of the target sequences to which the probes of the present invention hybridize.

As previously mentioned, according to another embodiment, a cocktail comprising two or more of the probes are employed to detect whether at least one oncogenic HPV type is present in a test sample. Most preferably, the cocktail is a component of an amplification reaction mixture where all of the probes of the present invention are part of the cocktail. The probes are hybridized with the amplification products to form complexes and any complexes are then detected as an indication of whether at least one oncogenic HPV type was present in the test sample. Most preferably, cocktails according to the present invention will contain at least SEQ ID NO 37 or its complement SEQ ID NO 38, and SEQ ID NO 40 or its complement SEQ ID NO 41.

The probes of the present invention can be provided as part of a kit useful for detecting the presence of at least one oncogenic HPV type in a test sample. The kits comprise one or more suitable containers containing one or more sequences according to the present invention, an enzyme having polymerase activity, and deoxynucleotide triphosphates. Typically, at least one sequence bears a label, but detection is possible without this.

The following examples are provided to further illustrate the present invention and not intended to limit the invention.

EXAMPLES

The following examples demonstrate detection of oncogenic strains of human papillomaviruses (HPV) using primers to amplify the target sequences and the probes herein provided. These DNA primers and probes are identified as SEQUENCE ID NO. 1, SEQUENCE ID NO. 2, SEQUENCE ID NO. 4, SEQUENCE ID NO. 7, SEQUENCE ID NO. 10, SEQUENCE ID NO. 13, SEQUENCE ID NO. 16, SEQUENCE ID NO. 19, SEQUENCE ID NO. 22, SEQUENCE ID NO. 25, SEQUENCE ID NO. 28, and SEQUENCE ID NO. 31, SEQUENCE ID NO. 34, SEQUENCE ID NO. 37 and SEQUENCE ID NO. 40. All the above primers and probes are specific for a region in the L1 gene of HPV. In the following examples SEQUENCE ID NOs. 1 and 2 are used as consensus amplification primers specific for this region in oncogenic and non-oncogenic types of HPV. A portion of the L1 sequence in oncogenic HPV Type 16 is designated herein as SEQ ID NO. 3. SEQ ID NO. 4 is used as a type-specific internal hybridization probe for oncogenic HPV Type 16. A portion of the L1 sequence in oncogenic HPV Type 18 is designated herein as SEQ ID NO. 6. SEQ ID NO. 7 is used as a type-specific internal hybridization probe for oncogenic HPV Type 18. A portion of the L1 sequence in oncogenic HPV Type 31 is designated herein as SEQ ID NO. 9. SEQ ID NO. 10 is used as a type-specific internal hybridization probe for oncogenic HPV Type 31. A portion of the L1 sequence in oncogenic HPV Type 33 is designated herein as SEQ ID NO. 12. SEQ ID NO. 13 is used as a type-specific internal hybridization probe for oncogenic HPV Type 33. A portion of the L1 sequence in oncogenic HPV Type 35 is designated herein as SEQ ID NO. 15. SEQ ID NO. 16 is used as a type-specific internal hybridization probe for oncogenic HPV Type 35. A portion of the L1 sequence in oncogenic HPV Type 39 is designated herein as SEQ ID NO. 18. SEQ ID NO. 19 is used as a type-specific internal hybridization probe for oncogenic HPV Type 39. A portion of the L1 sequence in oncogenic HPV Type 45 is designated herein as SEQ ID NO. 21. SEQ ID NO. 22 is used as a type-specific 20 internal hybridization probe for oncogenic HPV Type 45. A portion of the L1 sequence in oncogenic HPV Type 51 is designated herein as SEQ ID NO. 24. SEQ ID NO. 25 is used as a type-specific internal hybridization probe for oncogenic HPV Type 51. A portion of the L1 sequence in oncogenic HPV Type 52 is designated herein as SEQ ID NO. 27. SEQ ID NO. 28 is used as a type-specific internal hybridization probe for oncogenic HPV Type 52. A portion of the L1 sequence in oncogenic HPV Type 56 is designated herein as SEQ ID NO. 30. SEQ ID NO. 31 is used as a type-specific internal hybridization probe for oncogenic HPV Type 56. A portion of the L1 sequence in oncogenic HPV Type 58 is designated herein as SEQ ID NO. 33. SEQ ID NO. 34 is used as a type-specific internal hybridization probe for oncogenic HPV Type 58. A portion of the L1 sequence in oncogenic HPV Type 59 is designated herein as SEQ ID NO. 36. SEQ ID NO. 37 is used as a type-specific internal hybridization probe for oncogenic HPV Type 59. A portion of the L1 sequence in oncogenic HPV Type 68 is designated herein as SEQ ID NO. 39. SEQ ID NO. 40 is used as a type-specific internal hybridization probe for oncogenic HPV Type 68.

Example 1

Preparation of HPV Primers and Probes

A. L1 Consensus Primers

Target-specific consensus primers were designed to detect the HPV L1 target sequence of oncogenic and non-oncogenic HPV types by oligonucleotide hybridization PCR. These primers were SEQ ID NO. 1 and SEQ ID NO. 2. Primer sequences were synthesized using standard oligonucleotide synthesis methodology and haptenated with adamantane at their 5' ends using standard cyanoethyl phosphoramidite coupling chemistry as described in U.S. Pat. No. 5,424,414 incorporated herein by reference.

B. L1 HPV Type-specific Probes The detection probes were designed to hybridize with the amplified HPV L1 target sequence by oligonucleotide hybridization. These probes are SEQ ID NO. 4 for HPV Type 16, SEQ ID NO. 7 for HPV Type 18, SEQ ID NO. 10 for HPV Type 31, SEQ ID NO. 13 for HPV Type 33, SEQ ID NO. 16 for HPV Type 35, SEQ ID NO. 19 for HPV Type 39, SEQ ID NO. 22 for HPV Type 45, SEQ ID NO. 25 for HPV Type 51, SEQ ID NO. 28 for HPV Type 52, SEQ ID NO. 31 for HPV Type 56, SEQ ID NO. 34 for HPV Type 58, SEQ ID NO. 37 for HPV Type 59 and SEQ ID NO. 40 for HPV Type 68. Probe SEQ ID NOs. 7, 10, 22, 25, 28, 31, 34, 37 and 40 were synthesized using standard oligonucleotide synthesis methodology and haptenated with 2 carbazoles at the 5' end using standard cyanoethyl phosphoramidite coupling chemistry as described in U.S. Pat. No. 5,464,746 (herein incorporated by reference), and blocked with phosphate at the 3' end. Probe SEQ ID NOs. 4, 13, 16 and 19 were synthesized using standard oligonucleotide synthesis methodology and haptenated with 2 carbazoles at the 3' end using standard cyanoethyl phosphoramidite coupling chemistry as described in U.S. Pat. No. 5,464,746. Reactivity was assessed against a known standard of HPV DNA.

Example 2

Sensitivity of HPV Detection

Plasmids, individually comprising the 13 oncogenic HPV types (HPV 16, 18, 31, 33, 35, 39, 45, 51, 52, 56, 58, 59 and 68) were prepared using the Qiagen Plasmid Kit (Qiagen Inc., Chatsworth, Calif.) according to the manufacturers instructions. In particular, for each plasmid, individual bacterial cultures containing the plasmids were grown overnight in 500 ml of TB media (1.2% bacto-trypton, 2.4% bacto-yeast extract, 0.4% v/v glycerol, 17 mM $KH_2PO_4$, 72 mM $K_2HPO_4$, 50 μg/ml ampicilin). The cells were collected by centrifugation (4° C., 10 minutes at 6000×g) and the pellet was resuspended in 10 ml of 50 mM Tris-HCl, 50 mM EDTA, 100 μg/ml RNase A (pH 8.0). 10 ml of 0.2 N NaOH, 1% SDS was then added to the resuspended pellet and the resulting solution was incubated at room temperature for 5 minutes. After the incubation period, 10 ml of 3 M KAc (pH 5.5) was added to the solution and this solution was then incubated on ice for 20 minutes. After incubation, cellular debris was removed from the mixtures by centrifugation (4° C., 30 minutes at 15,000×g) and the resulting supernatants were loaded onto a QIAGEN-tip 500 (Qiagen Inc.), equilibrated with 10 ml of 750 mM NaCl, 50 mM MOPS, 15% ethanol, 0.15% Triton® X-100 (pH 7.0). The QIAGEN-tip 500 was washed twice with 1.0 M NaCl, 50 mM MOPS, 15% ethanol (pH 7.0) before the DNA was eluted with 1.25 M NaCl, 50 mM MOPS, 15% ethanol, 0.15% Triton® X-100 (pH 8.5). DNA was precipitated from the eluant with 0.7 volumes of isopropanol and recovered by centrifugation (4° C., 30 minutes at 15,000×g). The DNA pellets were washed with 15 ml of cold 70% ethanol, air dried for 5 minutes and dissolved in 500 μl TE buffer (10 mM tris (hydroxymethyl) aminomethane (Tris®), 1 mM ethylenediamene tetraacetic acid (EDTA), pH 8.0).

The HPV plasmids were quantitated by comparison to a known DNA standard (linear M13 rf DNA from New England Biolabs, Beverly, Mass.) using agarose gel electrophoresis. To accomplish this the SYBR Green 1 (Molecular Probes, Eugene Oreg.) fluorescence of the standards and HPV samples was measured with an IS-1000 digital imaging system (Alpha Innotech, San leandro Calif.) and the HPV plasmid concentration calculated from the M13 standard curve.

Separate dilution sets of the purified HPV DNAs were PCR amplified and detected using the HPV consensus primers (SEQ ID NOs. 1 and 2) and the HPV detection probes (SEQ ID NOs. 4, 7, 10, 13, 16, 19, 22, 25, 28, 31, 34, 37 and 40 for HPV types 16, 18, 31, 33, 35, 39, 45, 51, 52, 56, 58, 59 and 68, respectively) described in Example 1. PCR extension was performed using 10 mM Tris-HCl, pH 8.3, 50 mM KCl, 0.5 mM EDTA, 10 μg/ml Bovine Serum Albumin (BSA) and 0.04% $NaN_3$. Taq polymerase was used at a concentration of 3.75 unitsand nucleotides were added giving a final concentration of 0.4 mM each. Primers were used at a concentration of 0.5 μM each, with probes for HPV types 51, 52, 56, 58 and 68 used at 3 μM, for HPV types 18 and 31 used at 4.5 μM, for HPV type 59 used at 6 μM and for HPV types 16, 33, 35, 39 and 45 used at 12 μM. A final concentration of 7 mM $MgCl_2$ was added at the same time as the sample. Testing was done using 50 μl of sample in a total reaction volume of 0.2 ml, with samples tested in duplicate using salmon testis DNA as a negative control.

Reaction mixtures were amplified in a Perkin-Elmer 480 Thermal Cycler. The following cycling conditions were used: 94° C. for 2 minutes followed by cycling at 95° C. for 20 seconds/44° C. for 1.5 minutes/72° C. for 1 minute for 5 cycles, then 95° C. for 5 seconds/54° C. for 30 seconds/72° C. for 15 seconds for 40 cycles, then 72° C. for 4 minutes. After the reaction mixtures were thermal cycled, the mixtures were maintained at 97° C. for 2 minutes and probe oligo hybridization was accomplished by rapidly lowering the temperature to 4° C.

After the reaction products reached 4° C. they were detected on the Abbott LCx® system (available from Abbott Laboratories, Abbott Park, Ill.). A suspension of anti-carbazole antibody coated microparticles and an anti-adamantane antibody/alkaline phosphatase conjugate (all of which are commercially available from Abbott Laboratories, Abbott Park, Ill.) were used in conjunction with the LCx® to capture and detect the reaction products. The average values from this experiment (calculated as counts/second/second; c/s/s) are presented in TABLE 2 and show the sensitivity of detection of different oncogenic HPV types to be approximately $10^3$ to $10^4$ molecules of DNA depending on the type.

TABLE 2

| HPV Type | Molecules of HPV DNA (LCx ® Rate: c/s/s) | | | | | | |
|---|---|---|---|---|---|---|---|
| | 0 | $10^3$ | $10^4$ | $10^5$ | $10^6$ | $10^7$ | $10^8$ |
| HPV 16 | 96.7 | 307 | 1043.8 | 1266.5 | 1141.5 | 1001.7 | 993.4 |
| HPV 18 | 100.6 | 1022.9 | 1345.2 | 1397.9 | 1361.4 | 1320.8 | 1256.8 |
| HPV 31 | 99.0 | 262.8 | 970.0 | 1336.8 | 1344.2 | 1369.8 | 1282.7 |
| HPV 33 | 103.8 | 280.9 | 896.2 | 963.2 | 846.0 | 665.4 | 654.6 |
| HPV 35 | 100.5 | 303.9 | 1003.3 | 887.0 | 735.8 | 740.5 | 647.7 |
| HPV 39 | 100.2 | 296.4 | 823.7 | 1009.3 | 899.5 | 733.4 | 640.5 |
| HPV 45 | 94.2 | 429.7 | 923.7 | 1067.5 | 962.0 | 943.1 | 998.9 |
| HPV 51 | 95.9 | 158.3 | 539.6 | 878.7 | 968.9 | 952.7 | 949.1 |
| HPV 52 | 100.1 | 112.0 | 415.5 | 1146.4 | 1257.8 | 1167.9 | 1029.6 |

TABLE 2-continued

| HPV Type | Molecules of HPV DNA (LCx ® Rate: c/s/s) | | | | | | |
|---|---|---|---|---|---|---|---|
| | 0 | $10^3$ | $10^4$ | $10^5$ | $10^6$ | $10^7$ | $10^8$ |
| HPV 56 | 98.8 | 643.6 | 1100.8 | 1162.9 | 11244 | 1061.1 | 1157.2 |
| HPV 58 | 104.4 | 306.3 | 1153.7 | 1463.3 | 1495.3 | 1520.6 | 1502.4 |
| HPV 59 | 100.3 | 546.8 | 785.7 | 863.4 | 990.5 | 984.7 | 1014.8 |
| HPV 68 | 86.4 | 279.1 | 349.6 | 1000.7 | 1011.9 | 899.5 | 877.7 |

Example 3

Specificity of HPV Detection

In addition to the 13 plasmids of oncogenic types of HPV obtained in Example 2, 12 plasmids of non-oncogenic types of HPV (HPV 6, 11, 13, 26, 32, 40, 42, 54, 55, 57, 61 and 66) were obtained.

DNA was purified from these plasmids as in Example 2 and diluted to $10^8$ molecules of DNA/reaction. The HPV consensus primers (SEQ ID NOs. 1 and 2) and the HPV detection probes (SEQ ID NOs. 4, 7, 10, 13, 16, 19, 22, 25, 28, 31, 34, 37 and 40 for HPV types 16, 18, 31, 33, 35, 39, 45, 51, 52, 56, 58, 59 and 68, respectively) described in Example 1 were used to amplify and detect the diluted DNA samples as described above in Example 2 except that the detection probes were used at a final concentration of 4 nM each in separate reactions to detect the amplification products produced by the HPV consensus primers. The data from this experiment is presented in TABLE 3 and shows specific amplification and detection of oncogenic types of HPV only, with the non-oncogenic types of HPV being non-reactive.

TABLE 3

| HPV Type | HPV Probe Type (LCx ® Rate c/s/s) | | | | | | | | | | | | |
|---|---|---|---|---|---|---|---|---|---|---|---|---|---|
| | 16 | 18 | 31 | 33 | 35 | 39 | 45 | 51 | 52 | 56 | 58 | 59 | 68 |
| Onc | | | | | | | | | | | | | |
| 16 | 1350 | – | – | – | – | – | – | – | – | – | – | – | – |
| 18 | – | 1291 | – | – | – | – | – | – | – | – | – | – | – |
| 31 | – | – | 1479 | – | – | – | – | – | – | – | – | – | – |
| 33 | – | – | – | 836 | – | – | – | – | – | – | – | – | – |
| 35 | – | – | – | – | 1211 | – | – | – | – | – | – | – | – |
| 39 | – | – | – | – | – | 1039 | – | – | – | – | – | – | – |
| 45 | – | – | – | – | – | – | 1015 | – | – | – | – | – | – |
| 51 | – | – | – | – | – | – | – | 1016 | – | – | – | – | – |
| 52 | – | – | – | – | – | – | – | – | 1049 | – | – | – | – |
| 56 | – | – | – | – | – | – | – | – | – | 1282 | – | – | – |
| 58 | – | – | – | 258 | – | – | – | – | – | – | 1249 | – | – |
| 59 | – | – | – | – | – | – | – | – | – | – | – | 1296 | – |
| 68 | – | – | – | – | – | – | – | – | – | – | – | – | 979 |
| Non-onc | | | | | | | | | | | | | |
| 6 | – | – | – | – | – | – | – | – | – | – | – | – | – |
| 11 | – | – | – | – | – | – | – | – | – | – | – | – | – |
| 13 | – | – | – | – | – | – | – | – | – | – | – | – | – |
| 26 | – | – | – | – | – | – | – | – | – | – | – | – | – |
| 32 | – | – | – | – | – | – | – | – | – | – | – | – | – |
| 40 | – | – | – | – | – | – | – | – | – | – | – | – | – |
| 42 | – | – | – | – | – | – | – | – | – | – | – | – | – |
| 54 | – | – | – | – | – | – | – | – | – | – | – | – | – |
| 55 | – | – | – | – | – | – | – | – | – | – | – | – | – |
| 57 | – | – | – | – | – | – | – | – | – | – | – | – | – |
| 61 | – | – | – | – | – | – | – | – | – | – | – | – | – |
| 66 | – | – | – | – | – | – | – | – | – | – | – | – | nt |

(Onc = oncogenic HPV types; Non-onc = non-oncogenic HPV types; A negative symbol (–) denotes tht the LCx ® rate was less than 120 c/s/s; nt = not tested.)

The data in Table 3 shows that the oncogenic HPV probes specifically detect the HPV types for which they are designed to detect.

Example 4

HPV Detection in Clinical Samples

A. Detection of HPV in Clinical Samples Using the HPV LCx® Assay and a Commercial Hybrid Capture Assay Ninety-eight clinical samples were tested for oncogenic HPV by Digene's Hybrid Capture Assay (Digene Diagnostics, Silver Spring, Md.) and compared to HPV detection using the HPV consensus primers (SEQ ID NOs. 1 and 2) and the HPV detection probes (SEQ ID NOs. 4, 7, 10, 13, 16, 19, 22, 25, 28, 31, 34, 37 and 40 for HPV types 16, 18, 31, 33, 35, 39, 45, 51, 52, 56, 58, 59 and 68, respectively) described in Example 1. Samples were collected in Digene sample buffer and processed according to the manufacturer's instructions. A portion of the sample was precipitated with ethanol at −70° C. and the pellet resuspended in 50 μl of 10 mM Tris, 1 mM EDTA, pH 8.0. Ten μl of this sample was then added to 90 μl of 50 mM EPPS (N-[2-Hydroxyethyl]Piperzaine-N'-[3-Propane Sulfonic Acid], pH 8.0 (Sigma Chemical Co., St. Louis, Mo.), 14 mM $MgCl_2$ and heated to 95–100° C. for 10 minutes. After cooling for 15 minutes to room temperature, sample was amplified and detected in a total reaction volume of 0.2 ml as in Example 2 (except $MgCl_2$ was added during sample preparation as stated above). Results are shown in Table 4.

TABLE 4

|  |  | HPV LCx ® Assay | |
|---|---|---|---|
|  |  | Positive | Negative |
| Digene Hybrid | Positive | 28 | 2 |
| Capture Assay | Negative | 20 | 48 |

In Table 4 above, 28 of 98 samples were HPV positive by both assays and 48 of 98 samples were HPV negative by both assays. The 2 samples identified as positive by the Digene assay but negative in the HPV LCx® assay were confirmed as negative in an alternate PCR assay performed at Johns Hopkins University where the clinical samples were obtained. Twenty samples were identified as HPV positive by the LCx® assay but were not detected by the Digene assay. Sixteen of these 20 samples were confirmed as positive in the assay at Johns Hopkins; the other 4 samples were retested as positive in the LCx® assay and typed as oncogenic using each probe in a separate reaction as in Example 3. Further proof of this was demonstrated by taking 14 of the Digene negative/LCx® positive samples, doing serial 10-fold dilutions from 1:10 to 1:1000 and testing these dilutions in the LCx® format. All 14 of these samples were detected at the highest 1:1000 dilution.

B. Detection of HPV in Biopsy Confirmed Cancer Specimens

Thirty-eight samples were obtained from patients with biopsy confirmed cancer. These samples were tested for oncogenic HPV by Digene's Hybrid Capture Assay (Digene Diagnostics, Silver Spring, Md.) and compared to HPV detection using the HPV consensus primers (SEQ ID NOs. 1 and 2) and the HPV detection probes (SEQ ID NOs. 4, 7, 10, 13, 16, 19, 22, 25, 28, 31, 34, 37 and 40 for HPV types 16, 18, 31, 33, 35, 39, 45, 51, 52, 56, 58, 59 and 68, respectively) described in Example 1. Samples were collected in Digene sample buffer and processed according to the manufacturers instructions. A portion of the sample was precipitated with ethanol at −70° C. and the pellet resuspended in 50 μl of 10 mM Tris, 1 mM EDTA, pH 8.0. Three μl of the sample was diluted in 97 μl of 10 mM Tris, pH 8.0, 14 mM $MgCl_2$ and heated to 95–100° C. for 10 minutes. After cooling for 15 minutes to room temperature, sample was amplified and detected in a total reaction volume of 0.2 ml as in Example 2 (except $MgCl_2$ was added during sample preparation as stated above). Results are shown in Table 5.

TABLE 5

|  |  | HPV LCx ® Assay | |
|---|---|---|---|
|  |  | Positive | Negative |
| Digene Hybrid | Positive | 18 | 0 |
| Capture Assay | Negative | 15 | 5 |

Both assays detect oncogenic HPV in 18 of 38 cancer specimens and both are negative for 5 of the 38 samples. These 5 samples were also found HPV negative by the Johns Hopkins alternate PCR assay. Fifteen of the cancer specimens were detected as containing oncogenic HPV by the LCX® assay but were negative in the Digene assay. However it should be noted that the Digene test does not include probes for 2 of the 15 LCX® positive/Digene negative subtypes detected (HPV types 39 and 58).

C. Detection of HPV in Biopsy Confirmed High Grade Cervical Interepithelial Neoplasia Specimens Twenty-two samples were obtained from patients with biopsy confirmed high grade cervical interepithelial neoplasia (H-CIN), prepared and tested as above in Example 4.B. comparing the HPV LCx® assay to Digene's Hybrid Capture Assay for detection of oncogenic HPV. Results are shown in Table 6.

TABLE 6

|  |  | HPV LCx ® Assay | |
|---|---|---|---|
|  |  | Positive | Negative |
| Digene Hybrid | Positive | 10 | 0 |
| Capture Assay | Negative | 9 | 3 |

Both assays detect oncogenic HPV in 10 of 22 H-CIN specimens and both are negative for 3 of the 22 samples. These 3 samples were also found HPV negative by the Johns Hopkins alternate PCR assay. Nine of the H-CIN specimens were detected as containing oncogenic HPV by the LCx® assay but were negative in the Digene assay. It should be noted that of these 9 discrepant samples, 2 contained an HPV type (HPV type 58) which is not tested for in the Digene assay.

While the invention has been described in detail and with reference to specific embodiments, it will be apparent to one skilled in the art that various changes and modifications may be made to such embodiments without departing from the spirit and scope of the invention.

What is claimed is:

1. An oligonucleotide cocktail for detecting the presence of oncogenic HPV types 16, 18, 31, 33, 35, 39, 45, 51, 52, 56, 58, 59 and 68 in a test sample, said cocktail including at least one oligonucleotide from each of the following sets:
   a) SEQ ID NO: 4 and SEQ ID NO:5,
   b) SEQ ID NO: 7 and SFQ ID NO:8,
   c) SEQ ID NO: 10 and SEQ ID NO: 11,
   d) SEQ ID NO: 13 and SEQ ID NO:14,
   e) SEQ ID NO: 16 and SEQ ID NO:17,
   f) SEQ ID NO: 19 and SEQ ID NO:20,
   g) SEQ ID NO: 22 and SEQ ID NO:23,
   h) SEQ ID NO:25 and SEQ ID NO:26,
   I) SEQ ID NO:28 and SFQ ID NO: 29,
   j) SEQ ID NO: 31 and SEQ ID NO: 32,
   k) SEQ ID NO: 34 and SEQ ID NO: 35,
   l) SEQ ID NO: 37 and SEQ ID NO: 38, and
   m) SEQ ID NO: 40 and SEQ ID NO: 41,
   wherein all oliognucleotides within the cocktail are labeled with the same label, and
   wherein the cocktail is capable of detecting the presence of oncogenic HPV types 16, 18 31, 22, 35, 39, 45, 51, 52, 56, 58, 59 and 68 in a test sample.

2. A method of detecting the presence of an oncogenic HPV type in a test sample comprising the steps of:
   a) contacting said test sample with an oligonucleotide cocktail claim 1; and
   b) detecting hybridization between a member of the cocktail and an oncogenic HPV type target sequence as an indication of the presence of an oncogenic HPV type in said sample.

3. A method for detecting the presence of at least one oncogenic HPV type in a test sample comprising the steps of:
   a) forming a reaction mixture comprising nucleic acid amplification reagents, at least one amplification primer for amplifying an oncogenic HPV target sequence, a test sample containing an ocogenic HPV type target sequence, and at least one oligonucleotide cocktail according to claim 1;
   b) subjecting said mixture to hybridization conditions to generate at least one nucleic acid sequence complementary to said target sequence;
   c) hybridizing said cocktail to said nucleic acid complementary to said target sequence so as to form a hybrid comprising an oligonucleotide from the cocktail and said nucleic acid; and
   d) detecting said hybrid as an indication of the presence of at least one oncogenic HPV type in said sample.

4. The method of claim 3 wherein the oligonucleotide of the cocktail are labeled with a capture label and said primer is labeled with a detection label.

5. The method of claim 3 wherein the oligonucleotide of the cocktail are labeled with a detection label and said primer is labeled with a capture label.

6. A kit comprising:
   a) at least one oligonucleotide cocktail according to claim 1, and
   b) amplification reagents.

* * * * *

SEQUENCE LISTING (1) GENERAL INFORMATION:

(iii) NUMBER OF SEQUENCES: 41

(2) INFORMATION FOR SEQ ID NO:1:

```
    (i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: synthetic DNA (xi) SEQUENCE DESCRIPTION: SEQ ID NO:1:

AAACAATGAC AACAACTATG ATG                                              23

(2) INFORMATION FOR SEQ ID NO:2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:2:

GAAAAATAAA CTGTAAATCA TATTC                                            25

(2) INFORMATION FOR SEQ ID NO:3:

(i) SEQUENCE CHARACTERISTICS:
        (A) LENGTH: 142 base pairs
        (B) TYPE: nucleic acid
        (C) STRANDEDNESS: single
        (D) TOPOLOGY: linear (ii) MOLECULE TYPE: genomic DNA (HPV type 16)

(xi) SEQUENCE DESCRIPTION: SEQ ID NO:3:

TTTGTTACTG TTGTTGATAC TACACGCAGT ACAAATATGT CATTATGTGC                 50

TGCCATATCT ACTTCAGAAA CTACATATAA AAATACTAAC TTTAAGGAGT                100

ACCTACGACA TGGGGAGGAA TATGATTTAC AGTTTATTTT TC                       142

(2) INFORMATION FOR SEQ ID NO: 4:

(i) SEQUENCE CHARACTERISTICS:
        (A) LENGTH: 18
        (B) TYPE:  nucleic acid
        (C) STRANDEDNESS:  single
        (D) TOPOLOGY:   linear (ii) MOLECULE TYPE: synthetic DNA (xi) SEQUENCE DESCRIPTION: SEQ ID NO: 4:

GCTGCCATAT CTACTTCA                                                    18

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:5:

TGAAGTAGAT ATGGCAGC                                                    18

(2) INFORMATION FOR SEQ ID NO:6:
```

(i) SEQUENCE CHARACTERISTICS:
    (A) LENGTH: 145 base pairs
    (B) TYPE: nucleic acid
    (C) STRANDEDNESS: single
    (D) TOPOLOGY: linear (ii) MOLECULE TYPE: genomic DNA (HPV type 18)

(xi) SEQUENCE DESCRIPTION: SEQ ID NO:6:

```
TTTGTTACTG TGGTAGATAC CACTCCCAGT ACCAATTTAA CAATATGTGC          50

TTCTACACAG TCTCCTGTAC CTGGGCAATA TGATGCTACC AAATTTAAGC         100

AGTATAGCAG ACATGTTGAG GAATATGATT TGCAGTTTAT TTTTC             145
```

(2) INFORMATION FOR SEQ ID NO:7:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:7:

```
GTAGCATCAT ATTGCC                                              16
```

(2) INFORMATION FOR SEQ ID NO:8:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: synthetic DNA (xi) SEQUENCE DESCRIPTION: SEQ ID NO:8:

```
GGCAATATGA TGCTAC                                              16
```

(2) INFORMATION FOR SEQ ID NO:9:

(i) SEQUENCE CHARACTERISTICS:
        (A) LENGTH: 142 base pairs
        (B) TYPE: nucleic acid
        (C) STRANDEDNESS: double
        (D) TOPOLOGY: linear (ii) MOLECULE TYPE: genomic DNA  (HPV type 31)

(xi) SEQUENCE DESCRIPTION: SEQ ID NO:9:

```
TTTGTTACTG TGGTAGATAC CACACGTAGT ACCAATATGT CTGTTTGTGC          50

TGCAATTGCA AACAGTGATA CTACATTTAA AAGTAGTAAT TTTAAAGAGT         100

ATTTAAGACA TGGTGAGGAA TTTGATTTAC AATTTATATT TC                 142
```

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:10:

```
GCAATTGCAA ACAGTGAT                                            18
```

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:11:

```
ATCACTGTTT GCAATTGC                                                     18
```

(2) INFORMATION FOR SEQ ID NO:12:

(i) SEQUENCE CHARACTERISTICS:
        (A) LENGTH: 139 base pairs
        (B) TYPE: nucleic acid
        (C) STRANDEDNESS: single
        (D) TOPOLOGY: linear (ii) MOLECULE TYPE: genomic DNA (HPV type 33)

(xi) SEQUENCE DESCRIPTION: SEQ ID NO:12:

```
TTTGTTACTG TGGTAGATAC CACTCGCAGT ACTAATATGA CTTTATGCAC                  50

ACAAGTAACT AGTGACAGTA CATATAAAAA TGAAAATTTT AAAGAATATA                 100

TAAGACATGT TGAAGAATAT GATCTACAGT TTGTTTTTC                             139
```

(2) INFORMATION FOR SEQ ID NO:13:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:13:

```
ATGCACACAA GTAACTAGT                                                    19
```

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:14:

```
ACTAGTTACT TGTGTGCAT                                                    19
```

(2) INFORMATION FOR SEQ ID NO:15:

(i) SEQUENCE CHARACTERISTICS:
        (A) LENGTH: 142 base pairs
        (B) TYPE: nucleic acid
        (C) STRANDEDNESS: single
        (D) TOPOLOGY: linear (ii) MOLECULE TYPE: genomic DNA (HPV type 35)

(xi) SEQUENCE DESCRIPTION: SEQ ID NO:15:

```
TTTGTTACTG TAGTTGATAC AACCCGTAGT ACAAATATGT CTGTGTGTTC                  50
```

```
TGCTGTGTCT TCTAGTGACA GTACATATAA AAATGACAAT TTTAAGGAAT          100

ATTTAAGGCA TGGTGAAGAA TATGATTTAC AGTTTATTTT TC                 142

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:16:

CTGCTGTGTC TTCTAGTG                                             18

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:17:

CACTAGAAGA CACAGCAG                                             18

(2) INFORMATION FOR SEQ ID NO:18:

(i) SEQUENCE CHARACTERISTICS:
        (A) LENGTH: 145 base pairs
        (B) TYPE: nucleic acid
        (C) STRANDEDNESS: single
        (D) TOPOLOGY: linear (ii) MOLECULE TYPE: genomic DNA (HPV type 39)

(xi) SEQUENCE DESCRIPTION: SEQ ID NO:18:

TTTCTTACTG TTGTGGACAC TACCCGTAGT ACCAACTTTA CATTATCTAC           50

CTCTATAGAG TCTTCCATAC CTTCTACATA TGATCCTTCT AAGTTTAAGG          100

AATATACCAG GCACGTGGAG GAGTATGATT TACAATTTAT ATTTC               145

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:19:

CTCTATAGAG TCTTCCATAC C                                         21

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: synthetic DNA
```

(xi) SEQUENCE DESCRIPTION: SEQ ID NO:20:

GGTATGGAAG ACTCTATAGA G                                              21

(2) INFORMATION FOR SEQ ID NO:21:

(i) SEQUENCE CHARACTERISTICS:
        (A) LENGTH: 145 base pairs
        (B) TYPE: nucleic acid
        (C) STRANDEDNESS: single
        (D) TOPOLOGY: linear (ii) MOLECULE TYPE: genomic DNA (HPV type 45)

(xi) SEQUENCE DESCRIPTION: SEQ ID NO:21:

TTTGTTACTG TAGTGGACAC TACCCGCAGT ACTAATTTAA CATTATGTGC                50

CTCTACACAA AATCCTGTGC CAAGTACATA TGACCCTACT AAGTTTAAGC                100

AGTATAGTAG ACATGTGGAG GAATATGATT TACAGTTTAT TTTTC                    145

(2) INFORMATION FOR SEQ ID NO:22:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:22:

CTACACAAAA TCCTGTG                                                   17

(2) INFORMATION FOR SEQ ID NO:23:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:23:

CACAGGATTT TGTGTAG                                                   17

(2) INFORMATION FOR SEQ ID NO:24:

(i) SEQUENCE CHARACTERISTICS:
        (A) LENGTH: 142 base pairs
        (B) TYPE: nucleic acid
        (C) STRANDEDNESS: single
        (D) TOPOLOGY: linear (ii) MOLECULE TYPE: genomic DNA (HPV type 51)

(xi) SEQUENCE DESCRIPTION: SEQ ID NO:24:

TTTATTACCT GTGTTGATAC TACCAGAAGT ACAAATTTAA CTATTAGCAC                50

TGCCACTGCT GCGGTTTCCC CAACATTTAC TCCAAGTAAC TTTAAGCAAT                100

ATATTAGGCA TGGGGAAGAG TATGAATTGC AATTTATTTT TC                       142

(2) INFORMATION FOR SEQ ID NO:25:

(i) SEQUENCE CHARACTERISTICS:
        (A) LENGTH: 15 base pairs
        (B) TYPE: nucleic acid (C) STRANDEDNESS: single
            (D) TOPOLOGY: linear (ii) MOLECULE TYPE: synthetic DNA (xi) SEQUENCE DESCRIPTION: SEQ ID NO:25:

CGGTTTCCCC AACAT                                                        15

(2) INFORMATION FOR SEQ ID NO:26:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: synthetic DNA (xi) SEQUENCE DESCRIPTION: SEQ ID NO:26:

ATGTTGGGGA AACCG                                                        15

(2) INFORMATION FOR SEQ ID NO:27:

(i) SEQUENCE CHARACTERISTICS:
            (A) LENGTH: 139 base pairs
            (B) TYPE: nucleic acid
            (C) STRANDEDNESS: single
            (D) TOPOLOGY: linear (ii) MOLECULE TYPE: genomic DNA (HPV type 52)

(xi) SEQUENCE DESCRIPTION: SEQ ID NO:27:

TTTGTCACAG TTGTGGATAC CACTCGTAGC ACTAACATGA CTTTATGTGC                  50

TGAGGTTAAA AAGGAAAGCA CATATAAAAA TGAAAATTTT AAGGAATACC                 100

TTCGTCATGG CGAGGAATTT GATTTACAAT TTATTTTTC                             139

(2) INFORMATION FOR SEQ ID NO:28:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: synthetic DNA (xi) SEQUENCE DESCRIPTION: SEQ ID NO:28:

GTGCTGAGGT TAAAAAG                                                      17

(2) INFORMATION FOR SEQ ID NO:29:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: synthetic DNA (xi) SEQUENCE DESCRIPTION: SEQ ID NO:29:

CTTTTTAACC TCAGCAC                                                      17

(2) INFORMATION FOR SEQ ID NO:30:

(i) SEQUENCE CHARACTERISTICS:
            (A) LENGTH: 139 base pairs
            (B) TYPE: nucleic acid

```
            (C) STRANDEDNESS: single
            (D) TOPOLOGY: linear (ii) MOLECULE TYPE: genomic DNA (HPV type 56)

(xi) SEQUENCE DESCRIPTION: SEQ ID NO:30:

TTTGTTACTG TAGTAGATAC TACTAGAAGT ACTAACATGA CTATTAGTAC              50

TGCTACAGAA CAGTTAAGTA AATATGATGC ACGAAAAATT AATCAGTACC             100

TTAGACATGT GGAGGAATAT GAATTACAAT TTGTTTTTC                         139

(2) INFORMATION FOR SEQ ID NO:31:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:31:

CTACAGAACA GTTAAGTAA                                                19

(2) INFORMATION FOR SEQ ID NO:32:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:32:

TTACTTAACT GTTCTGTAG                                                19

(2) INFORMATION FOR SEQ ID NO:33:

(i) SEQUENCE CHARACTERISTICS:
        (A) LENGTH: 139 base pairs
        (B) TYPE: nucleic acid
        (C) STRANDEDNESS: single
        (D) TOPOLOGY: linear (ii) MOLECULE TYPE: genomic DNA (HPV type 58)

(xi) SEQUENCE DESCRIPTION: SEQ ID NO:33:

TTTGTTACCG TGGTTGATAC CACTCGTAGC ACTAATATGA CATTATGCAC              50

TGAAGTAACT AAGGAAGGTA CATATAAAAA TGATAATTTT AAGGAATATG             100

TACGTCATGT TGAAGAATAT GACTTACAGT TTGTTTTTC                         139

(2) INFORMATION FOR SEQ ID NO:34:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:34:

AACTAAGGAA GGTACAT                                                  17

(2) INFORMATION FOR SEQ ID NO:35:
```

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:35:

ATGTACCTTC CTTAGTT                                                      17

(2) INFORMATION FOR SEQ ID NO:36:

(i) SEQUENCE CHARACTERISTICS:
        (A) LENGTH: 145 base pairs
        (B) TYPE: nucleic acid
        (C) STRANDEDNESS: single
        (D) TOPOLOGY: linear (ii) MOLECULE TYPE: genomic DNA (HPV type 59)

(xi) SEQUENCE DESCRIPTION: SEQ ID NO:36:

TTTTTAACAG TTGTAGATAC TACTCGCAGC ACCAATCTTT CTGTGTGTGC                   50

TTCTACTACT TCTTCTATTC CTAATGTATA CACACCTACC AGTTTTAAAG                  100

AATATGCCAG ACATGTGGAG GAATTTGATT TGCAGTTTAT ATTTC                       145

(2) INFORMATION FOR SEQ ID NO:37:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:37:

CTACTACTCT CTATTCCTAA TG                                                22

(2) INFORMATION FOR SEQ ID NO:38:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:38:

CATTAGGAAT AGAGAGTAGT AG                                                22

(2) INFORMATION FOR SEQ ID NO:39:

(i) SEQUENCE CHARACTERISTICS:
        (A) LENGTH: 145 base pairs
        (B) TYPE: nucleic acid
        (C) STRANDEDNESS: single
        (D) TOPOLOGY: linear (ii) MOLECULE TYPE: genomic DNA (HPV type 68)

(xi) SEQUENCE DESCRIPTION: SEQ ID NO:39:

TTTCTTACTG TTGTGGATAC CACTCGCAGT ACCAATTTTA CTTTGTCTAC                   50

TACTACTGAA TCAGCTGTAC CAAATATTTA TGATCCTAAT AAATTTAAGG                  100

```
-continued

AATATATTAG GCATGTTGAG GAATATGATT TGCAATTTAT ATTTC                    145

(2) INFORMATION FOR SEQ ID NO:40:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:40:

CTTTGTCTAC TACTACTGA                                                  19

(2) INFORMATION FOR SEQ ID NO:41:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:41:

TCAGTAGTAG TAGACAAAG                                                  19
```